United States Patent
Sauter et al.

(10) Patent No.: US 9,549,756 B2
(45) Date of Patent: Jan. 24, 2017

(54) MEDICAL INSERTION AID COMPRISING DRAWN INSERTION DUCT

(71) Applicant: Aesculap AG, Tuttlingen (DE)

(72) Inventors: Wolfgang Sauter, Renquishausen (DE); Manfred Dworschak, Dürbheim (DE); Axel Wittmer, Herford (DE)

(73) Assignee: Aesculap AG (DE)

( * ) Notice: Subject to any disclaimer, the term of this patent is extended or adjusted under 35 U.S.C. 154(b) by 11 days.

(21) Appl. No.: 14/413,751

(22) PCT Filed: Jul. 10, 2013

(86) PCT No.: PCT/EP2013/064614
§ 371 (c)(1),
(2) Date: Jan. 9, 2015

(87) PCT Pub. No.: WO2014/016123
PCT Pub. Date: Jan. 30, 2014

(65) Prior Publication Data
US 2015/0164547 A1    Jun. 18, 2015

(30) Foreign Application Priority Data
Jul. 26, 2012  (DE) .................. 10 2012 213 205

(51) Int. Cl.
*A61B 17/34* (2006.01)
*A61B 1/00* (2006.01)

(52) U.S. Cl.
CPC ....... *A61B 17/3421* (2013.01); *A61B 1/00154* (2013.01); *A61B 17/3474* (2013.01); *A61B 17/3417* (2013.01)

(58) Field of Classification Search
CPC ............... A61B 2017/3433; A61B 2017/3437; A61B 17/3417; A61B 17/34; A61B 17/0231
See application file for complete search history.

(56) References Cited

U.S. PATENT DOCUMENTS

| | | | |
|---|---|---|---|
| 2,604,685 A | * | 7/1952 | Harms ............ A61B 17/34 27/24.2 |
| 5,339,800 A | | 8/1994 | Wiita et al. |

(Continued)

FOREIGN PATENT DOCUMENTS

| | | |
|---|---|---|
| DE | 203 09 079 U1 | 8/2003 |
| DE | 102009033314 | 1/2011 |

(Continued)

OTHER PUBLICATIONS

International Search Report issued in related International Application No. PCT/EP2013/064614, dated May 20, 2014.

(Continued)

*Primary Examiner* — Eduardo C Robert
*Assistant Examiner* — Julianna N Harvey
(74) *Attorney, Agent, or Firm* — RatnerPrestia

(57) ABSTRACT

A medical insertion aid for surgical instruments and/or optical systems includes a shank forming an insertion duct, at the inner wall of which at least one groove extending in the longitudinal duct direction or being longitudinally orientated is formed. In addition or as an alternative, a medical insertion aid includes a distal end portion (axial central portion preferably in the distal end area) and a radially outwardly extending, preferably closed peripheral fluid flow inhibiting edge in the distal end portion. The inhibiting edge preferably forms at least one axially opening circular channel or groove, with the opening being directed distally and/or proximally.

10 Claims, 2 Drawing Sheets

(56) References Cited

U.S. PATENT DOCUMENTS

| | | | | |
|---|---|---|---|---|
| 5,575,756 A | * | 11/1996 | Karasawa | A61B 1/00068 600/121 |
| 6,733,479 B1 | | 5/2004 | Ott | |
| 2003/0045834 A1 | * | 3/2003 | Wing | A61B 17/34 604/161 |
| 2004/0230218 A1 | | 11/2004 | Criscuolo et al. | |
| 2009/0012362 A1 | | 1/2009 | Kucklick | |
| 2009/0192444 A1 | | 7/2009 | Albrecht et al. | |
| 2010/0042117 A1 | * | 2/2010 | Kim | A61B 17/0469 606/148 |
| 2011/0202065 A1 | | 8/2011 | Takizawa | |
| 2012/0053410 A1 | | 3/2012 | Torisawa | |
| 2012/0083661 A1 | * | 4/2012 | Rockrohr | A61B 17/3421 600/208 |
| 2014/0194685 A1 | | 7/2014 | Riek | |

FOREIGN PATENT DOCUMENTS

| | | |
|---|---|---|
| DE | 102011107615 | 1/2013 |
| FR | 2 900 562 A1 | 11/2007 |

OTHER PUBLICATIONS

German Search Report dated Mar. 22, 2013 in German Application No. 10 2012 213 205.8, including partial translation.
Chinese Office Action dated Sep. 5, 2016 for Chinese Application No. 201380039041.5, including English translation, 13 pages.

* cited by examiner

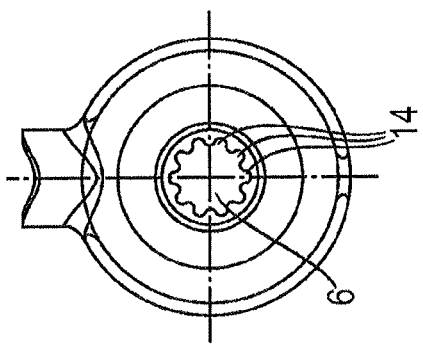
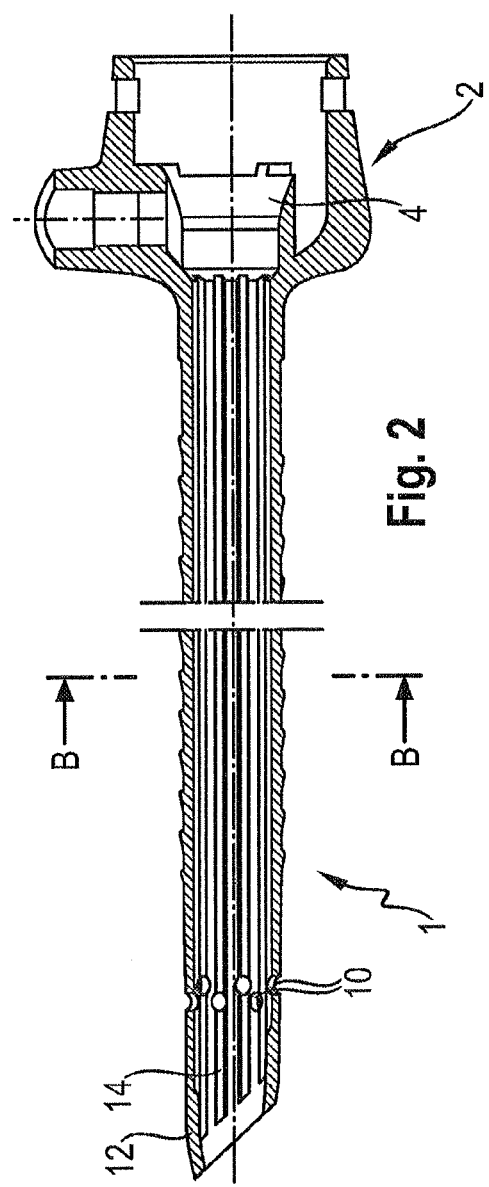
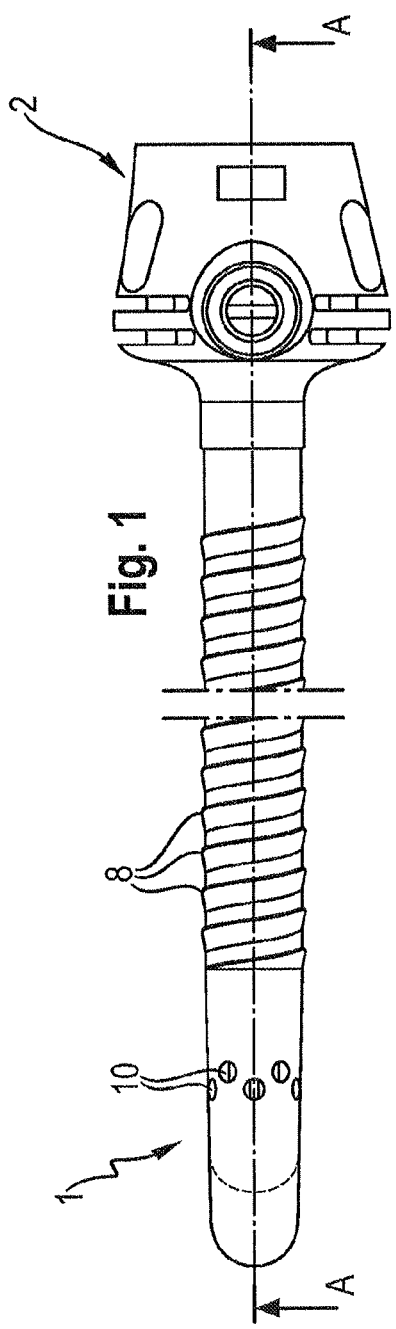

MEDICAL INSERTION AID COMPRISING DRAWN INSERTION DUCT

RELATED APPLICATIONS

This application is filed under 35 U.S.C. §371 as the U.S. National Phase of International Application No. PCT/EP2013/064614, filed Jul. 10, 2013, which in turn claims the benefit of priority of German Application No. DE 10 2012 213 205.8, filed Jul. 26, 2012, the contents of both applications being incorporated by reference herein for all purposes.

FIELD

The present invention relates to a trocar sleeve and, respectively, an insertion aid for surgical instruments (trocars, endoscopes etc.). In particular, the invention relates to a medical insertion aid comprising an insertion or working duct drawn at least in portions.

BACKGROUND

Insertion aids for surgical instruments are used especially for minimal-invasive interventions in a patient's body to insert surgical instruments and/or endoscopes into a (possibly artificially created) body cavity. Depending on the place and purpose of use, the advantage of said insertion aids consists in the fact that either only small access orifices by appropriate tissue cuts are required so as to introduce appropriate instruments into the patient's body or that no external injuries whatsoever are caused for example in the case of a coloscopic or gastroscopic application. In this respect, for the insertion aids in question rigid as well as flexural tube or hose elements are provided which on the inside form at least one insertion duct of a predetermined diameter for pushing through the surgical instrument/endoscope.

A special form of such insertion aid is the trocar. This is an instrument with the aid of which an access to a body cavity such as the abdominal or chest cavity is provided in a sharp or obtuse manner and is kept open by a trocar sleeve (tube). The obturator initially introduced into the trocar sleeve is a pin or rod which is supported to be axially movable in the tube and the point of which closes the tube aperture. After introducing the obturator-trocar unit into the body cavity the surgeon then has the option after removing the obturator from the trocar to inspect the body cavity by an optical system (endoscope), for example, through the trocar or to operate in the body cavity through the trocar by surgical clipping and/or cutting instruments.

The tubes/trocars especially for inspection of body cavities (laparoscopy, thoracoscopy, arthroscopy etc.) may have a valve mechanism, a connection for insufflating (blowing in) a gas or a rinsing fluid or other supplementary equipment at their respective proximal extracorporeal end portion.

It is known from the state of the art to usually employ in the case of conventional laparoscopic interventions, for example, endoscopes having an (outer) diameter of 10 mm in connection with corresponding (rigid) trocars/trocar sleeves (tubes). As a rule, also the gas insufflation for generating and/or maintaining a pneumoperitoneum beneath the abdominal wall is carried out via said optical trocars as they are called. The tolerances for providing an annular gap between the optical system (outer diameter of endoscope) and the inner diameter of the trocar sleeve usually are dimensioned so that a sufficient gas passage is possible through the same in order to at least compensate for gas leakage from the pneumoperitoneum and thus to maintain the body cavity expanded (under gas pressure).

The miniaturization of the accesses, especially of the diameter of the surgical and optical instruments used including an endoscope in general in laparoscopy or endoscopy, for example, is more and more in progress, however, so that so called "single port" or single incision" interventions are more widely used as an option of use of these miniaturized instruments. Usually in the umbilical fossa a skin incision of only about 2 cm in length is made. By such incision for instance three 5 mm trocars (trocar sleeves/tubes) are then introduced via individual fascia incisions.

This novel technology is consequently facilitated by the use of a 5 mm optical system (endoscope) which initially basically constitutes no technical problem as such, as these optical systems in the meantime almost correspond to a 10 mm model as regards both the image and resolution quality and the light sensitivity. Moreover, the light intensity of lighting bodies (LED) of the latest generation is very high and hence the heat development is comparatively low so that modern optical systems and light-sensitive sensors (CMOS chips) are not excessively thermally impaired.

However, due to the afore-mentioned miniaturization new problems occur at other positions of the afore-described insertion aid-instrument-system which have not been known so far in this way, at least have not had any detrimental effects on the surgical working cycles. These include inter alia the problems emphasized in the following:

1. Insufficient Gas Insufflation

The maximum distal gas passage when using a 5 mm optical system (endoscope), for example, in combination with a corresponding 5 mm trocar (tube) turns out to be borderline low and considerably restricts the generation/maintenance of a pneumoperitoneum. If the pneumoperitoneum is to be built up completely anew, valuable time gets lost or it is not possible at all. The reason for this basically consists in the fact that the cross-section of the annular gap between the trocar sleeve and the instrument inserted in the same (optical system) is too small with an instrument diameter of 5 mm (with corresponding oversize on the trocar sleeve side) so as to attain a sufficient gas volume flow which at least compensates for the gas leakage flow. That is to say that in this case a limit for miniaturization for the insertion aid-instrument-system is not constituted by the technical/constructional possibilities of miniaturization concerning the optical system (endoscope) but by simple flow-mechanical conditions.

In this respect, a known design variant provides to form the trocar sleeve at the distal end portion thereof including a radial constriction (contraction) at the inside matching the obturator or instrument diameter so as to generate in this way sort of a throttle for the gas flow and at the same time to reach an improved distal guide of the instrument inserted in the trocar sleeve (tube). Ahead of the radial constriction at the inside (in the proximal direction) the lumen of the feed passage inside the tube is radially expanded by several tenths of millimeters, however, so that an annular gap is formed between an inserted instrument and the trocar sleeve.

So that sufficient gas can exhaust via the trocar into the body cavity despite the arrangement of the afore-described radial constriction or contraction at the distal end of the trocar sleeve, a number of lateral exit bores are introduced in the trocar sleeve partially closely (proximally) ahead of the constriction/contraction from which exit bores gas may escape laterally (in the radial direction) into the pneumoperitoneum. Since, however, the gas must flow through the still narrow annular gap proximally relative to the radial exit orifices, the exiting maximum gas volume flow remains to be basically limited.

2. Relatively Heavy Stains of the Optical System

With a 2 cm incision according to the foregoing description usually smaller blood vessels are injured which result in a minor seeping haemorrhage at least temporarily after introducing the trocars. Gradually one or more drops of blood and tissue fluid accumulate at the distal point (distal leading edge) of the trocar sleeve. If the optical system (endoscope) protruding at the distal trocar sleeve end is now pulled out of or retracted from the trocar sleeve for cleaning the lens, for example, which is necessary from time to time in order to remove precipitation obstructing the view (the latter is formed after a particular OP period by the use of HF or ultrasonic application, for instance), the blood/tissue fluid drop adhering to the leading edge is also sucked into the trocar sleeve and stains/covers the latter at the inside of its duct wall. If now the cleaned optical system (endoscope) is now re-introduced into the trocar sleeve (having a small annular gap dimension), thus the fluid adhering at the inside is stripped off at least in parts and thus immediately stains at least the border of the lens again.

Although in the 10 mm optical systems (endoscopes) common so far this problem basically arises as well, but it is definitely weakened for the following reasons, however:

When the optical system (endoscope) is pushed forward again, due to the larger annular gap width between the optical system (endoscope) and the trocar sleeve more fluid is retained in the annular gap and thus does not at all get onto the optical system (or the lens).

Due to the larger optical system (lens) proportionally a smaller (border-side) area of the optical system or lens is stained, wherein this staining has only little influence on the performance of the optical system.

SUMMARY

In view of these problems, it is the object of the present invention to ensure sufficient gas flow. Preferably also measures should be taken to reduce the staining of the optical system. It is a special objective to achieve the afore-mentioned object without the outer diameter of the trocar sleeve being increased substantially (or not at all) and without the distal internal lumen of the sleeve being expanded. The latter is especially important, because otherwise such gap width occurs between the obturator (or the instrument introduced) and the inner diameter of the trocar sleeve that fascia tissue, for example, might be drawn into the annular gap especially upon introducing the trocar/ instrument.

The object according to the invention as well as the further objectives are achieved by an insertion aid in accordance with the invention. Advantageous configurations and further developments are also described in accordance with the invention.

According to a first aspect of the present invention, the medical insertion aid for surgical instruments and/or optical systems (endoscopes) includes a shank (trocar sleeve/tube) forming or having an insertion duct (working duct) at the inner wall of which at least one groove orientated (extending) in the longitudinal direction of the duct is formed. The at least one groove can extend linearly in the axial direction of the shank or can extend longitudinally in spiral, zigzag shape or otherwise (at least in portions).

By the at least one groove so-to-speak a locally radially expanded (additional) flow duct for introducing and/or discharging gas/fluid is provided the cross-section of which is substantially independent of the general diameter of the feed duct and thus of the annular gap width and in this way ensures sufficient gas volume flow. Since the at least one groove only partially requires a thinned material at the shank, the stability characteristic thereof is largely retained vis-à-vis a shank having no groove. A thickening of the shank wall vis-à-vis a groove-less shank (according to the state of the art) is not necessary or necessary only to a minor extent. Finally the at least one groove does not influence the guiding function of the shank with respect to the introduced surgical instrument/optical system (endoscope).

In accordance with another aspect of the present invention, a plurality of grooves can be formed preferably at an equal peripheral distance from each other at the inner wall of the insertion duct. Thus each of the groove cross-sections can be reduced, wherein in their entirety a sufficient volume flow still can be produced. Moreover, the weakening of the shank wall is thus further decreased.

It may be of advantage when the at least one groove or the plurality of grooves runs out (ends) before the distal shank end is reached. In this case fascia tissue can be prevented from being drawn into the at least one groove or grooves especially when the trocar/insertion aid is introduced into the patient's cavity. This result optionally can be even improved when in the distal end portion of the shank a radial constriction or contraction narrows the insertion duct preferably over the entire periphery thereof, wherein in this case the at least one groove or the plurality of grooves (continuously or abruptly) run out proximally relative to the constriction/contraction or in an axial central portion of the constriction/contraction.

In accordance with another aspect of the present invention, especially when a radial constriction/contraction is provided at the distal end portion of the insertion duct (not restricted thereto), a number of radial through bores (at least one) may be provided in the distal end portion of the shank as well as preferably at a proximal distance from the radial constriction, the through bores radially (fluid-) communicating the insertion duct with the local shank environment. In this way, the gas volume flow does not or only slightly exhaust at the distal shank point but is deflected into the radial through bores so as to then exhaust on the side of the shank out of the feed passage (comprising the annular gap and the at least one groove).

Preferably the number of radial through bores is arranged in the peripheral direction (equally) spaced apart from each other and, further preferably, is orientated and/or placed such that the through bores open into the grooves at the inner wall of the insertion duct and intersect the same, respectively. Thus the gas volume flow guided through the grooves can be guided almost unhindered into the through bores so that pressure losses can be reduced.

It can be especially favorable in this context when the through bores are preferably alternately offset in the axial direction and form two or more (axially spaced) peripheral rows. In this case it is of advantage when the through bores arranged to be axially offset relative to each other are overlapping in the peripheral direction. Especially by reason of the axially offset arrangement of the through bores a flat discharge gas jet substantially closed in the peripheral direction and directed radially to all sides can be generated which can act like a (pneumatic) barrier or shield against liquid (drops) flowing along the outside of the shank in dependence on the gas exhaust velocity (and thus in dependence on the cross-sections of the through bores). It is possible in this way to avoid already in advance that a liquid drop forms at the distal leading edge of the shank which drop is then sucked into the at least one groove.

In accordance with another aspect of the invention, the medical insertion aid for surgical instruments and/or optical systems (endoscopes) may include a shank (trocar sleeve/tube) forming or having an insertion duct (working duct). In an axial central portion of the shank, preferably in the area of its distal end the shank has at its outer periphery a radially outwardly protruding flow inhibiting edge extending preferably in ring shape (further preferably as a closed ring or subdivided in ring segments) around the shank. At this inhibiting edge the liquid draining at the outside of the shank accumulates (possibly forming individual drops) and is thus prevented from flowing further in the direction of the distal shank point.

Preferably the flow inhibiting edge may form at least one groove or channel shaped undercut that opens axially in the proximal and/or distal direction. In other words, the flow inhibiting edge is L, U, V, X or H shaped in cross-section, thereby forming preferably jointly with the peripheral shank wall at least one (or two) channels that open either in the distal direction or in the proximal direction or simultaneously in both axial directions (in the case of the X or H shape).

The channel opened in the proximal direction thus forms sort of a liquid collecting channel in which draining liquid may accumulate. The channel width is preferably selected so that in the channel gap a capillary effect occurs, thereby the liquid draining (in the distal direction) being so-to-speak sucked into the channel gap. The channel opened in the distal direction, on the other hand, at its radially outer (free) edge forms primarily a drain edge from which draining liquid which possibly forms drops can freely drip off. The latter effect can be even intensified in that radially opening gas exit orifices (preferably according to the foregoing description) are arranged in the area of the flow inhibiting edge, i.e. directly distally with respect to the flow inhibiting edge but still inside the flow field of the exiting gas, said orifices being adapted to assist dripping of liquid.

In order to facilitate overflowing of the fluid flow inhibiting edge with a peripheral groove opened in the distal direction the inhibiting edge is continuously transformed (without forming any step) in the proximal direction into the outside of the shank and thus constitutes no (significant) obstruction to flow at this axial position.

BRIEF DESCRIPTION OF THE DRAWING FIGURES

Hereinafter the invention shall be illustrated in detail by way of preferred embodiments with reference to the accompanying figures:

FIG. 1 shows the side view of a medical/surgical instrument insertion aid according to a first preferred embodiment of the present invention;

FIG. 2 shows the longitudinal section of the instrument insertion aid along the line of cut A-A according to FIG. 1;

Figure 4:
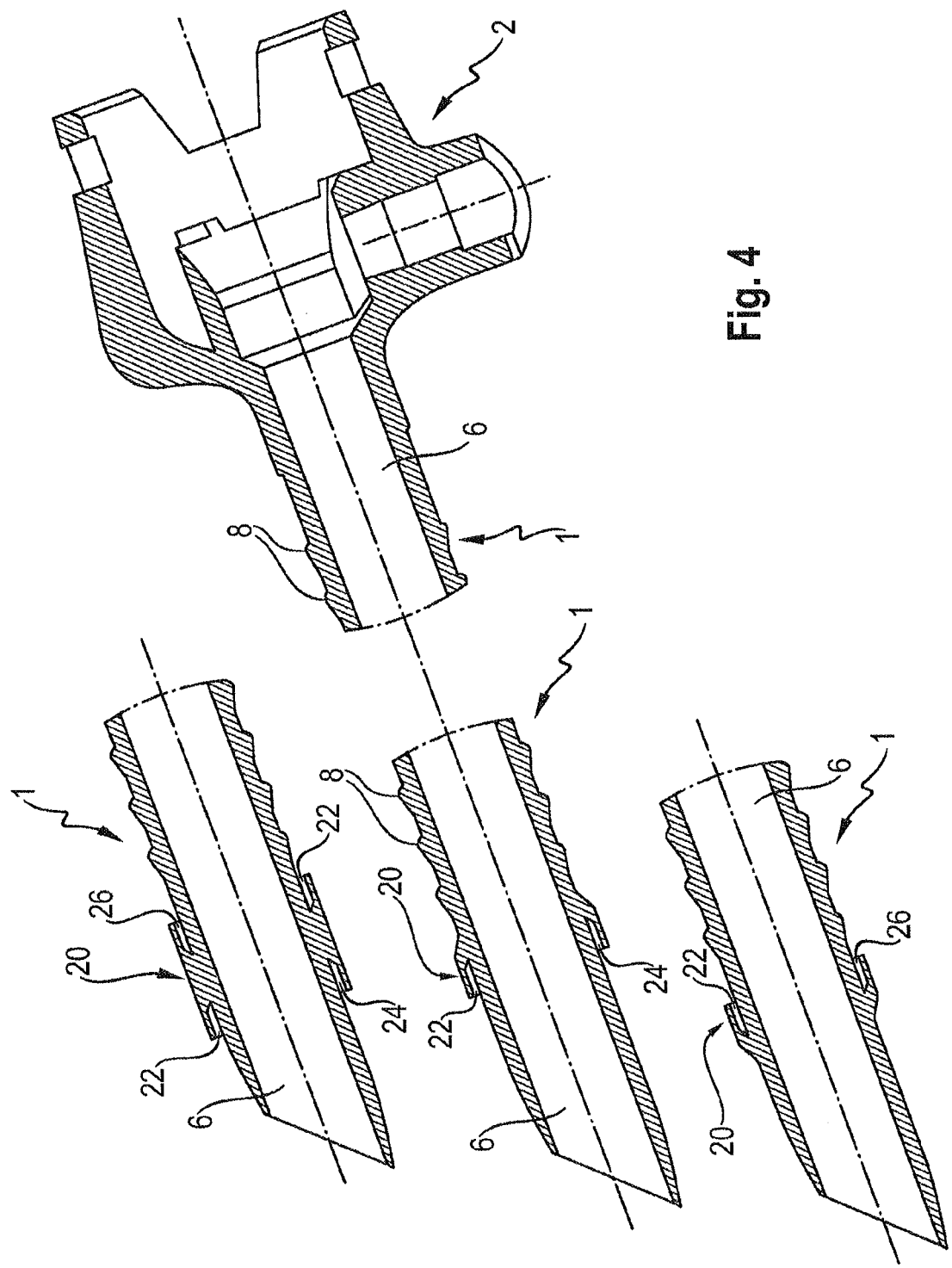

FIG. 3 shows the cross-section of the instrument insertion aid along the line of cut B-B according to FIG. 2; and FIG. 4 shows the longitudinal section of an instrument insertion aid according to a second preferred embodiment of the present invention, wherein in this context it is already referred to the fact that the technical features of the first embodiment described hereinafter (although not shown in FIG. 3) may also be realized in the instrument insertion aid of the second embodiment.

DETAILED DESCRIPTION

The instrument insertion aid according to the invention in the present case is a rigid trocar comprising a shank-like trocar sleeve 1 the distal end face of which is beveled relative to the trocar axis and at the proximal end portion of which a connecting piece 2 for various supplementary equipment such as at least one insufflating device (not shown in detail) is disposed. Moreover, the connecting piece 2 according to FIG. 2 forms an inserting orifice 4 in axial extension to the shank 1 through which surgical and/or optical instruments such as an endoscope (not shown in detail) can be inserted into and removed from the shank 1 and a duct 6 formed in the latter, respectively. In the present case, the connecting piece 2 is attached/screwed onto the shank 1, i.e. tightly connected to the shank 1. It is also imaginable, however, that the shank 1 and the connecting piece 2 are integrally formed of the same material. It is further possible that the connection between the shank 1 and the connecting piece 2 is detachable so as to combine different connecting pieces with different shanks (with equal outer shank diameters).

In accordance with the present embodiment, the insertion aid concretely is a trocar or a tube (trocar sleeve). It is also possible, however, that the illustrated shank 1 consists of flexural tube material as it might be used in the case of gastroscopy or coloscopy. According to FIG. 1, the shank 1 further includes on the outside a number of axially spaced (wedge-shaped) peripheral shoulders 8 or a spirally extending (wedge-shaped) peripheral ledge, each forming a stop face in the proximal direction and being tapered in the distal direction. In this way the tube can be introduced into the body cavity of a patient while sliding over the peripheral shoulders 8, the peripheral shoulders blocking and, resp., obstructing independent (inadvertent) slipping out of the body cavity due to the stop faces acting in the proximal direction.

Finally the shank/tube 1 exhibits in its distal end portion a number of through bores/holes 10 (equally) spaced in the peripheral direction and radially extending through the shank wall for fluid-communicating the insertion duct 6 formed inside the shank 1 (cf. FIG. 2) with the local shank environment. As is shown especially in FIG. 1, the radial through bores 10 are preferably alternately offset in the axial direction and in this way form at least two (or more) axially spaced peripheral bore rows. The through bores/through holes 10 are round bores in the present case each having such diameter that the bores 10 of the two axially spaced rows are not overlapping so that between the respective adjacent bores 10 of the same row just as between two adjacent bores 10 of different rows there is always remaining a shank material web of predetermined web width. In this way the material weakening of the shank 1 in this area is kept low and the shank stability is largely retained. Alternatively to this, it is also possible, however, that the through holes 10 of the two rows are overlapping viewed in the axial direction.

As can be inferred especially from FIG. 2, the insertion duct 6 has a radial constriction 12 or a radially inwardly protruding and closed peripheral contraction, resp., in an axial portion between the distal shank end and the radial through holes 10, thereby the diameter of the insertion duct being reduced in this area so that an instrument (or obturator) inserted in the insertion duct 6 is guided in an approximately sliding manner at this distal constriction/contraction 12. The constriction 12 extends in the axial direction of the (trocar) shank 1 up to the distal end face thereof.

Finally, the shank 1 includes at the inner wall of the guiding duct at least one, according to FIG. 3 preferably a plurality of longitudinal grooves 14 (evenly) spaced in the peripheral direction which in the present case extend linearly in the axial direction and before reaching the distal end face of the shank 1 preferably end or run out in the area of the constriction 12. By the run-out of the grooves 14 (about 2-3 mm ahead of the distal shank point) a smooth transition is generated so that an instrument/obturator can be pushed through the insertion duct 6 without getting jammed. The groove/grooves 14 is/are arranged so that they intersect the radial through holes 10 and in this way have a direct fluid communication with the through holes 10. Alternatively it is also possible, however, to form the grooves 14 not linearly but inclined with respect to the shank axis, in spiral or in zigzag shape. In this context it is crucial that the shank wall is not excessively weakened by the groove(s) 14 in this area so that the shank stability is not lastingly modified vis-à-vis a standard shank (which is not drawn). Also, the groove depth should be selected such that the outer diameter of the shank according to the invention approximately corresponds to that of the (not drawn) standard shank.

The function of the insertion aid according to the invention can be summarized as follows:

When the shown trocar sleeve (shank) comprising an already inserted obturator or surgical instrument (optical system) is inserted into a body cavity, it is basically possible that blood and/or tissue fluid drains at the outside of the shaft in the distal direction and accumulates in drop shape at the distal shank point/edge. Since, however, for insufflation of the body cavity a gas is continuously passed through an annular gap (not shown in detail) between the instrument/obturator and the (trocar) shank 1 as well as mainly through the at least one groove 14 or the grooves 14 in a sufficient amount (sufficiently high gas volume per time unit) to the through holes 10 and from there exhausts radially outwardly, (possibly depending on the exhaust velocity as well as the distance of the respective adjacent exhaust orifices 10) sort of a gas jet curtain/wall (preferably substantially closed in peripheral direction) can be built up which is adapted to act so-to-speak as flow barrier/brake for the blood/tissue fluid mixture in the axial direction (pneumatic drop barrier). In this manner, already in advance drop formation of blood/tissue fluid can be counteracted at the distal shank point at least to a certain extent.

When the obturator or the surgical instrument (optical system, endoscope) is retracted from the insertion aid, i.e. from the (trocar) shank 1, the condition that a probably still present residual fluid drop is sucked into the annular gap between the obturator/instrument/optical system and the trocar sleeve may occur. However, in this case the drop fluid does not migrate over the entire inner duct wall but preferably attaches substantially to the longitudinal grooves 14. When consequently the instrument/optical system is shifted in the distal direction again, it may be possible to largely retain the fluid in the groove(s) 14 so that the optical system is not or not drastically stained. But this also means that the afore-mentioned optional function of the radial gas exhaust orifices as (pneumatic) drop barrier/brake basically is not necessary, as distally accumulating fluid drops possibly do not or only to a minor extent get into the annular gap.

Basically, the design of the at least one longitudinal groove 14 on the inside of the insertion duct 6 preferably in connection with the radial gas exhaust orifices 14 is easy to manufacture and therefore advantageously suited especially for single-use trocars, for example made of plastic material. An efficient improvement of the gas flow is reached by the same, while the outer diameter remains substantially unchanged.

FIG. 4 illustrates a second embodiment of an insertion aid according to the invention of this species, wherein only those technical features are illustrated by which the second embodiment differs from the afore-described first embodiment of the invention. Hence it is basically possible to provide all or selected features of the first embodiment, such as the inner longitudinal groove(s) and/or the radial gas exhaust orifices, also in the insertion aid according to FIG. 4.

The medical instrument insertion aid according to FIG. 4 equally consists of the shank 1 and the connecting piece 2 connected/formed distally thereto. The inserting or working duct 6 for medical instruments (not shown) is indicated in the shank 1 (equipped with longitudinal groove(s), where appropriate), the duct opening toward the atmosphere at the distal end of the shank 1. Although it is not illustrated in more detail, the shank 1 may be formed to include radial discharge orifices/bores and/or inner longitudinal duct groove(s) according to the first preferred embodiment.

At the outer periphery as well as in an axial central portion of the shank 1, preferably in the area of its distal end, a presently closed peripheral, radially protruding fluid flow inhibiting edge 20 is arranged/formed that differs as to its shape and/or its radial extension (as is shown in FIG. 4) from the (flaky) projecting edges 8 which are preferably formed to be axially spaced from each other equally at the outer shank periphery but which have only the function of supporting the shank 1 in the patient's cavity and are not adapted to (effectively) stop draining fluid, however.

The fluid flow inhibiting edge 20 in the present case is L, U, V, X or H shaped in cross-section, thereby the inhibiting edge 20 forming between itself and the outside of the shank at least one peripheral groove or channel 22 which is axially open in the distal and/or proximal direction. From the selected opening direction of the peripheral groove/channel different inhibiting effects are resulting, as will be described hereinafter:

1. Peripheral Channel Having an Aperture in the Distal Direction

In this case the fluid flow inhibiting edge 20 forms a free peripheral (separation) edge 24 while an axial peripheral groove 22 with the groove aperture in the direction of the distal shank end is formed. This free (flow separation) edge 24 serves as drop accumulating edge at which draining liquid accumulates preferably in drop shape and independently drips upon reaching a particular drop size (drop weight). This dripping operation can be assisted, where necessary, by the radial gas discharge orifices 10 which may be preferably placed in direct axial connection in the distal direction relative to the fluid flow inhibiting edge 20 (such that the inhibiting edge 20 and especially the separation edge 24 are still in the exhaust field of the discharge orifices 10).

Moreover, it is optionally possible to select the gap width of the groove 22 so that sort of a capillary effect on the fluid can be generated hereby so as to quasi suck the fluid into the groove opposed to its flow direction and thus prevent it from continuing to flow.

2. Peripheral Channel Having an Aperture in the Proximal Direction

In this case the fluid flow inhibiting edge 20 constitutes a free peripheral (introducing) edge 26 while forming an axial peripheral groove 22 having a groove aperture in the direction of the proximal shank end. This groove/channel 22 consequently is (peripherally) opened in the direction opposed to the fluid flow direction and thus serves as a kind of collecting channel for the draining fluid. The groove depth of this groove 22 opened to the proximal direction hence is selected so that sufficient fluid can be received therein which, according to experience, forms within the scope of a patient's treatment.

In this case, too, it is optional to select the gap width of the groove 22 so that a kind of capillary effect on the fluid can be generated so as to quasi suck the fluid into the groove and in this way to prevent inadvertent escape especially when the maximum groove fill level is reached.

It is finally mentioned that only one channel (in this case in L, U or V shape) or two channels having channel apertures in different axial directions (in this case in X or H shape) may be provided. There is also the possibility of arranging two (or more) channels having the same orientation of aperture at an axial distance from each other.

Summing up, a medical insertion aid for surgical instruments and/or optical systems is disclosed comprising a shank 1 forming an insertion duct 6 at the inner wall of which at least one groove 14 extending in the longitudinal duct direction or being longitudinally orientated is formed. In addition or alternatively a medical insertion aid is disclosed which in its distal end portion of the shank (axial central portion preferably in the distal end area) has a radially outwardly extending, preferably closed peripheral fluid flow inhibiting edge. Furthermore this inhibiting edge preferably forms at least one axially opening circular channel or groove having a distal and/or proximal opening direction.

The invention claimed is:

1. A medical insertion aid for surgical instruments and/or optical systems, the medical insertion aid comprising:
a shank forming an insertion duct, the insertion duct comprising an inner wall, wherein at least one groove extending in a longitudinal duct direction or being longitudinally oriented is formed at the Inner wall of the insertion duct, the shank including in its axial central and/or distal end portion at least one radially outwardly extending fluid flow inhibiting edge that extends in a closed ring shape around the shank and is of one-piece with the shank, wherein the at least one radially outwardly extending fluid flow inhibiting edge forms at least one axially opening circular channel, the channel comprising an opening that is directed distally and/or proximally, and wherein the channel inhibits the flow of fluid by sucking fluid into the channel by capillary action.

2. The medical insertion aid according to claim 1, wherein the at least one groove comprises a plurality of grooves formed at the inner wall of the insertion duct, the grooves separated from one another by an equal circumferential distance.

3. The medical insertion aid according to claim 1, wherein the at least one groove runs out before it reaches the distal end portion of the shank.

4. The medical insertion aid according to claim 3, wherein the distal end portion of the shank, a radial constriction or contraction narrows the insertion duct over the entire periphery thereof, the at least one groove running out proximally relative to the constriction or contraction, or in the axial central portion thereof.

5. The medical insertion aid according to claim 4, further comprising a plurality of radial through bores in the distal end portion of the shank, the through bores arranged at a proximal distance from the radial constriction and connecting the insertion duct to the local shank environment.

6. The medical insertion aid according to claim 5, wherein the through bores are evenly spaced from each other in the peripheral direction and are orientated and/or placed so that they open into the at least one groove at the inner wall of the insertion duct or intersect the at least one groove.

7. The medical insertion aid according to claim 5, wherein the through bores are alternately offset from each other in an axial direction.

8. The medical insertion aid according to claim 7, wherein the through bores comprise respective axially offset through bores, the respective axially offset through bores overlapping one another in the peripheral direction.

9. The medical insertion aid according to claim 1, wherein the opening of the channel is directed distally, and the at least one radially outwardly extending fluid flow inhibiting edge forms a peripheral free flow drain edge.

10. The medical insertion aid according to claim 1, wherein the opening of the channel is directed proximally, and the at least one radially outwardly extending fluid flow inhibiting edge forms a peripheral free flow introducing edge.

* * * * *